United States Patent [19]

Maurer et al.

[11] 4,162,320

[45] Jul. 24, 1979

[54] COMBATING ARTHROPODS WITH N,N-DIALKYL-O-(4-DIALKYLAMINO-PYRIMIDIN-2-yl)-CARBAMIC ACID ESTERS

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 915,623

[22] Filed: Jun. 14, 1978

[30] Foreign Application Priority Data

Jul. 5, 1977 [DE] Fed. Rep. of Germany ....... 2730273

[51] Int. Cl.$^2$ .................... A61K 31/505; C07D 239/34

[52] U.S. Cl. ...................................... 424/251; 544/317

[58] Field of Search .......................... 544/317; 424/251

[56] References Cited

U.S. PATENT DOCUMENTS

| | | | |
|---|---|---|---|
| 2,694,712 | 11/1954 | Gysin et al. | 544/319 |
| 3,627,891 | 12/1971 | Driscoll | 544/317 |

FOREIGN PATENT DOCUMENTS

| | | | |
|---|---|---|---|
| 1181657 | 2/1970 | United Kingdom | 544/320 |

*Primary Examiner*—Donald G. Daus

*Assistant Examiner*—James H. Turnipseed

*Attorney, Agent, or Firm*—Sprung, Felfe, Horn, Lynch & Kramer

[57] ABSTRACT

An N,N-Dialkyl-O-(4-dialkylamino-pyrimidin-2-yl)-carbamic acid ester of the formula

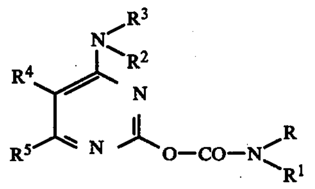

in which R, $R^1$, $R^2$ and $R^3$ each independently is alkyl, $R^4$ is hydrogen, alkyl, alkylthio or halogen, and $R^5$ is hydrogen or alkyl, which possess arthropodicidal properties.

9 Claims, No Drawings

COMBATING ARTHROPODS WITH N,N-DIALKYL-O-(4-DIALKYLAMINO-PYRIMIDIN-2-yl)-CARBAMIC ACID ESTERS

The present invention relates to and has for its objects the provision of particular new N,N-dialkyl-O-(4-dialkylamino-pyrimidin-2-yl)-carbamic acid ester which possess anthropodicidal properties, active compositions in the form of mixtures of such compounds with solid and liquid dispersible carrier vehicles, and methods for producing such compounds and for using such compounds in a new way especially for combating pests, e.g., arthropods, with other and further objects becoming apparent from a study of the within specification and accompanying examples.

It is already known that certain N,N-dimethyl-O-pyrimidinyl-carbamic acid esters, for example N,N-dimethyl-O-(2-isopropyl-6-methyl-pyrimidin-4-yl)- or -O-(2-dimethylamino-6-methyl-pyrimidin-4-yl)-carbamic acid ester, possess insecticidal properties (see U.S. Pat. No. 2,694,712 and British Pat. No. 1,181,657).

The present invention now provides, as new compounds, the N,N-dialkyl-O-pyrimidinyl-carbamic acid esters of the general formula

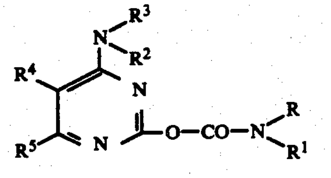

(I)

in which

R, $R^1$, $R^2$ and $R^3$, which need not be identical, each represent alkyl, $R^4$ represents hydrogen, alkyl, alkylthio or halogen and $R^5$ represents hydrogen or alkyl.

Preferably, R, $R^1$, $R^2$ and $R^3$ represent identical, straight-chain or branched alkyl with 1 to 6 carbon atoms (especially methyl or ethyl), $R^4$ represents hydrogen, chlorine, or straight-chain or branched alkyl or alkylthio with, in either case, 1 to 4 carbon atoms (especially with 1 or 2 carbon atoms), and $R^5$ represents hydrogen or straight-chain or branched alkyl with 1 to 4 (especially 1 or 2) carbon atoms.

Surprisingly, the N,N-dialkyl-O-pyrimidinyl-carbamic acid esters according to the invention possess a better insecticidal action than compounds of analogous structure, and of the same type of action, previously known from the literature. The compounds according to the present invention thus represent a genuine enrichment of the art.

The present invention also provides a process for the preparation of an N,N-dialkyl-O-pyrimidinyl-carbamic acid ester (I) in which a 2-hydroxy-4-dialkylamino-pyrimidine of the general formula

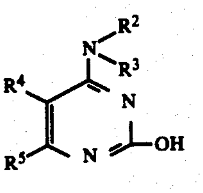

(II), in which $R^2$ to $R^5$ have the above-mentioned meanings, (a) is reacted, either in the form of an alkali metal salt or alkaline earth metal salt or as such in the presence of an acid acceptor, with an N,N-dialkyl-carbamic acid halide of the general formula

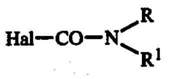

(III), in which

R and $R^1$ have the above-mentioned meanings and

Hal represents halogen, preferably chlorine, if appropriate in the presence of a diluent, or (b) is reacted, if appropriate in the presence of a diluent, with phosgene, and subsequently with an amine of the general formula

(IV), in which R and $R^1$ have the above-mentioned meanings, if appropriate in the presence of an acid acceptor.

If, for example, 2-hydroxy-4-dimethylamino-5-chloro-pyrimidine and N,N-diethyl-carbamic acid chloride are used as starting materials in process variant (a), the course of the reaction can be represented by the following equation:

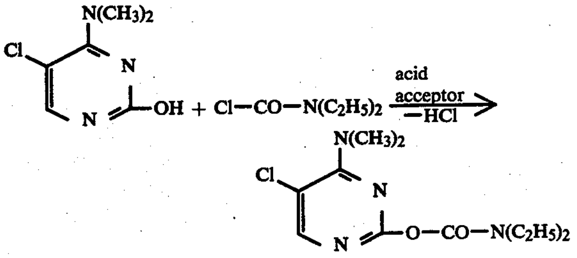

If, for example 2-hydroxy-4-dimethylamino-pyrimidine, phosgene and dimethylamine are used as starting materials in process variant (b), the course of the reaction can be represented by the following equation:

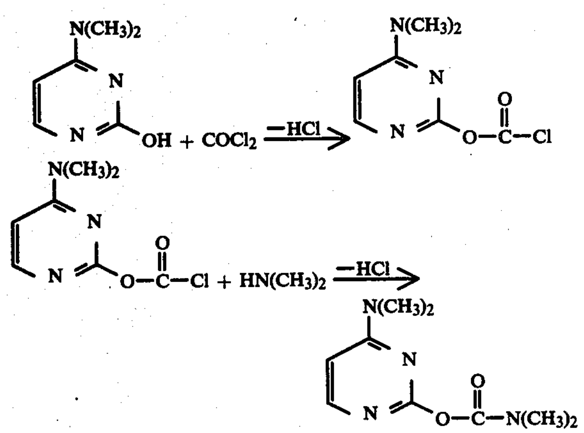

The 2-hydroxy-4-dialkylamino-pyrimidines (II) to be used as starting materials can be prepared in accordance with processes known from the literature; where $R^4$ represents hydrogen, alkyl or halogen, they can be prepared from the corresponding 2-halogen compounds by saponification, and where $R^4$ represents alkylthio, they can be prepared from the corresponding 2-hydroxy-pyrimidines which are unsubstituted in the 5-position, dimethyl disulphide and sulphuryl chloride, if appropriate in the presence of a solvent.

The following may be mentioned as specific examples of the 2-hydroxy-4-dialkylamino-pyrimidines (II): 2-hydroxy-4-dimethylamino-pyrimidine, 2-hydroxy-4-diethylamino-pyrimidine, 2-hydroxy-4-dimethylamino-5-chloropyrimidine, 2-hydroxy-4-dimethylamino-5-methyl-pyrimidine, 2-hydroxy-4-dimethylamino-6-methyl-pyrimidine, 2-hydroxy-4-dimethylamino-5-methylthio-pyrimidine, 2-hydroxy-4-dimethylamio-5-ethylthio-pyrimidine, 2-hydroxy-4-dimethylamino-5,6-dimethyl-pyrimidine, 2-hydroxy-4-dimethylamino-5-methylamino-6-methyl-pyrimidine, 2-hydroxy-4-dimethylamino-5-chloro-6-methyl-pyrimidine, 2-hydroxy-4-diethylamino-5-chloro-pyrimidine, 2-hydroxy-4-diethylamino-5-methyl-pyrimidine, 2-hydroxy-4-diethylamino-6-methyl-pyrimidine, 2-hydroxy-4-diethylamino-5-methylthio-pyrimidine, 2-hydroxy-4-diethylamino-5-ethylthio-pyrimidine, 2-hydroxy-4-diethylamino-5,6-dimethylpyrimidine, 2-hydroxy-4-diethylamino-5-methylthio-6-methyl-pyrimidine and 2-hydroxy-4-diethylamino-5-chloro-6-methyl-pyrimidine.

The N,N-dialkyl-carbamic acid halides (III) and the amines (IV), which are also to be used as starting materials, are known from the literature and can be readily prepared in accordance with customary methods. As specific examples of these compounds there may be mentioned: N,N-dimethyl- and N,N-diethyl-carbamic acid chloride, and dimethylamine and diethylamine.

Process variants (a) and (b) for the preparation of the compounds according to the invention are preferably carried out in the presence of a suitable diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate, potassium carbonate, sodium methylate, sodium ethylate, potassium methylate and potassium ethylate, have proved particularly suitable, as have aliphatic, aromatic or hetrocyclic amines, for example trimethylamine, triethylamine, dimethylaniline, dimethylbenzylamine and pyridine.

The reaction temperature can be varied within a substantial range. In general, the reaction is carried out at from 0° to 100° C., preferably at from 30° to 80° C.

In general, the reaction is allowed to take place under normal pressure.

To carry out process variant (a), the carbamic acid halide component is preferably employed in 10 to 30% excess. The reactants are in most cases mixed in an organic solvent in the presence of an acid acceptor and boiled under reflux. If necessary, insoluble matter is filtered off and the filtrate is concentrated.

The new compounds are obtained in a crystalline form and are characterized by their melting point.

As already mentioned, the N,N-dialkyl-O-pyrimidinyl-carbamic acid esters according to the invention are distinguished by an excellent insecticidal activity.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Demalinea spp.;

from the order of the Thysanoptera, for example *Hercinothrips femoralis* and Thrips tabaci;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon co-*

*chleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp.; *Monomorium pharaonis* and Vespa spp.;

from the order of the Diptera, for example Aedes spp., Anopholes spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating composition for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The 2-hydroxy-4-dialkylamino-pyrimidines (II) to be used as starting materials could be prepared, for example, as follows:

EXAMPLE 1

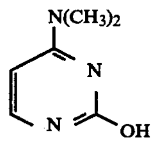

(a)

15.8 g (0.1 mol) of 2-chloro-4-dimethylamino-pyrimidine (for its preparation, see J. Chem. Soc. Perkin Trans. II, 1972, page 457) were boiled with 16.4 g (0.2 mol) of sodium acetate in 100 ml of glacial acetic acid for 4 hours under reflux. The solvent was then distilled off in vacuo, 150 ml of water were added to the residue, and this mixture was again evaporated. The residue was dissolved in 150 ml of water and extracted with 3 times 100 ml of chloroform. The organic phases were dried over sodium sulphate and the solvent was then distilled off in vacuo. 9.3 g (68% of theory) of 2-hydroxy-4-dimethylamino-pyrimidine remained in the form of colorless crystals of melting point 242° C.

The following compounds could be prepared analogously to (a):

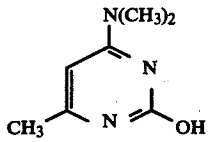

(b)

in 88% yield, and with melting point 265° C.

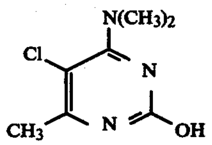

(c)

in 51% yield, and with melting point 234° C.

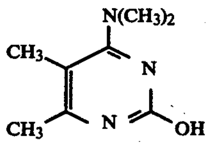

(d)

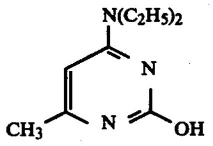

(e)

in 89% yield and with melting point 208° C.

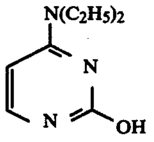

(f)

EXAMPLE 2

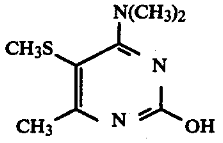

(a)

6.8 g (0.05 mol) of sulphuryl chloride were added in the course of 30 minutes to a solution of 4.7 g (0.05 mol) of dimethyl disulphide in 150 ml of methylene chloride at −20° C. After 20 minutes, this solution was added dropwise, at −10° C., to a suspension of 17 g (0.1 mol) of the sodium salt of 2-hydroxy-4-dimethylamino-6-methyl-pyrimidine in 200 ml of methylene chloride. The mixture was then stirred for a further 18 hours at room temperature. The solution was thereafter extracted with 200 ml of water, the organic phase was dried over sodium sulphate and the solvent was distilled off in vacuo. 8.8 g (45% of theory) of 2-hydroxy-4-dimethylamino-5-methylthio-6-methyl-pyrimidine remained in the form of colorless crystals of melting point 209° C.

The following compound could be prepared analogously to (a):

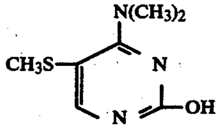

b)

The novel arthropodicides could be prepared as follows:

EXAMPLE 3

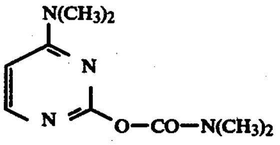

(1)

A mixture of 14 g (0.1 mol) of 2-hydroxy-4-dimethylaminopyrimidine, 16.6 g (0.12 mol) of potassium carbonate, 200 ml of chloroform and 12.8 g (0.12 mol) of N,N-dimethylcarbamic acid chloride was boiled for 20 hours under reflux. The insoluble matter was then filtered off and the filtrate was evaporated in vacuo. 17.6 g (84% of theory) of N,N-dimethyl-O-[4-dimethylamino-pyrimidin-2-yl]-carbamic acid ester remained in the form of light brown crystals of melting point 92° C.

The following compounds of the general formula

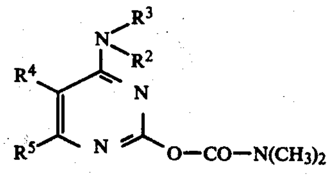

(Ia)

could be prepared analogously:

TABLE 1

| Compound No. | $R^2$ | $R^3$ | $R^4$ | $R^5$ | Yield (% of theory) | Melting point (°C.) |
|---|---|---|---|---|---|---|
| 2 | $CH_3$ | $CH_3$ | H | $CH_3$ | 89 | 134 |
| 3 | $CH_3$ | $CH_3$ | Cl | $CH_3$ | 43 | 74 |
| 4 | $CH_3$ | $CH_3$ | $SCH_3$ | $CH_3$ | 82 | 66 |
| 5 | $C_2H_5$ | $C_2H_5$ | H | $CH_3$ | 88 | 70 |
| 6 | $CH_3$ | $CH_3$ | $CH_3$ | $CH_3$ | | |
| 7 | $C_2H_5$ | $C_2H_5$ | H | H | | |

The insecticidal activity of the compounds of this invention is illustrated by the following examples wherein the compounds according to the present invention are each identified by the number (given in brackets) from the preparative examples hereinabove.

The known comparison compounds are identified as follows:

(A) = 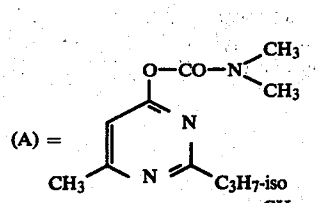

(B) = 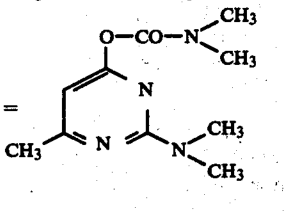

EXAMPLE 4

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 2

(insects which damage plants)
*Myzus* test

| Active compound | Active compound concentration in % | Degree of destruction after 1 day |
|---|---|---|
| (A) | 0.1 | 100 |
| | 0.01 | 50 |
| | 0.001 | 0 |
| (1) | 0.1 | 100 |
| | 0.01 | 100 |
| | 0.001 | 70 |

Table 2-continued (insects which damage plants)
*Myzus* test

| Active compound | Active compound concentration in % | Degree of destruction after 1 day |
|---|---|---|
| (2) | 0.1 | 100 |
| | 0.01 | 100 |
| | 0.001 | 40 |
| (4) | 0.1 | 100 |
| | 0.01 | 100 |
| | 0.001 | 85 |

EXAMPLE 5

Root-systemic action

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 3

(root-systemic action)
*Myzus persicae*

| Active compound | Degree of destruction in % at an active compound concentration of 5 ppm |
|---|---|
| (A) | 0 |
| (B) | 0 |
| (2) | 100 |
| (1) | 100 |
| (4) | 100 |
| (5) | 100 |

It will be appreciated that the instant specification and examples are set forth by way of illustration and not limitation, and that various modifications and changes may be made without departing from the spirit and scope of the present invention.

What we claim is:

1. An N-N-dialkyl-O-(4-dialkylamino-pyrimidin-2-yl)-carbamic acid ester of the formula

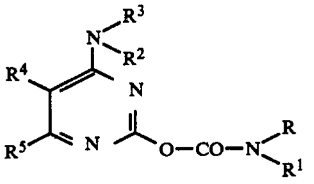

in which

R, $R^1$, $R^2$ and $R^3$ each independently is alkyl with 1 to 6 carbon atoms, $R^4$ is hydrogen, alkyl or alkylthio each with 1 to 4 carbon atoms, or halogen, and $R^5$ is hydrogen or alkyl with 1 to 4 carbon atoms.

2. An ester according to claim 1, in which $R^4$ is hydrogen, chlorine, or alkyl or alkylthio each with 1 to 4 carbon atoms.

3. An ester according to claim 1, in which said ester is N,N-dimethyl-O-(4-dimethylamino-pyrimidin-2-yl)-carbamic acid ester of the formula

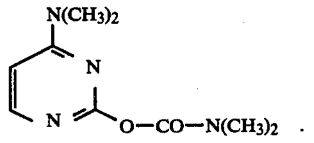

4. An ester according to claim 1, in which said ester is N,N-dimethyl-O-(4-dimethylamino-6-methyl-pyrimidin-2-yl)-carbamic acid ester of the formula

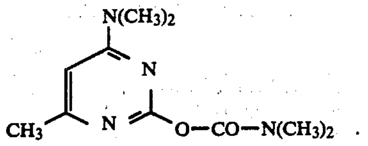

5. An ester according to claim 1, in which said ester is N,N-dimethyl-O-(5-chloro-4-dimethylamino-6-methyl-pyrimidin-2yl)-carbamic acid ester of the formula

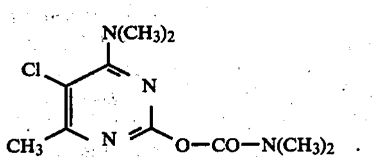

6. An ester according to claim 1, in which said ester is N,N-dimethyl-O-(4-dimethylamino-6-methyl-5-methylmercapto-pyrimidin-2-yl)-carbamic acid ester of the formula

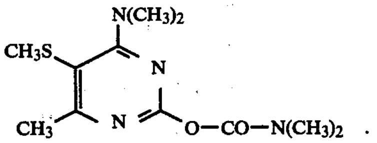

7. An arthropodicidal composition containing as active ingredient an arthropodicidally effective amount of an ester according to claim 1 in admisture with a diluent.

8. A method of combating arthropods which comprises applying to the arthropods, or to a habitat thereof, an arthropodicidally effective amount of an ester according to claim 1.

9. The method according to claim 8, in which said ester is

N,N-dimethyl-O-(4-dimethylamino-pyrimidin-2-yl)-carbamic acid ester,

N,N-dimethyl-O-(4-dimethylamino-6-methyl-pyrimidin-2-yl)-carbamic acid ester,

N,N-dimethyl-O-(5-chloro-4-dimethylamino-6-methyl-pyrimidin-2-yl)-carbamic acid ester, N,N-dimethyl-O-(4-dimethylamino-6-methyl-5-methylmercapto-pyrimidin-2-yl)-carbamic acid ester.

* * * * *